United States Patent [19]

Roninson et al.

[11] Patent Number: 5,206,352
[45] Date of Patent: Apr. 27, 1993

[54] COMPOSITIONS FOR CLONES CONTAINING DNA SEQUENCES ASSOCIATED WITH MULTIDRUG RESISTANCE IN HUMAN CELLS

[75] Inventors: Igor B. Roninson, Chicago, Ill.; Ira H. Pastan, Potomac; Michael M. Gottesman, Bethesda, both of Md.

[73] Assignee: Board of Trustees of the University of Illinois, Urbana, Ill.

[21] Appl. No.: 622,836

[22] Filed: Sep. 24, 1990

Related U.S. Application Data

[63] Continuation of Ser. No. 892,575, Aug. 1, 1986, abandoned, which is a continuation-in-part of Ser. No. 845,610, Mar. 28, 1986, abandoned.

[51] Int. Cl.$^5$ .................. C07H 21/00; C12Q 1/68
[52] U.S. Cl. ........................ 536/24.31; 435/6; 435/69.1; 435/91; 435/172.3; 935/9; 935/17; 935/78
[58] Field of Search ............ 435/6, 91, 172.3, 69.1; 536/27; 935/78, 9, 17; 514/44

[56] References Cited

U.S. PATENT DOCUMENTS

| | | | |
|---|---|---|---|
| 4,675,283 | 6/1987 | Roninson | 935/78 X |
| 4,837,306 | 6/1989 | Ling et al. | 530/387 |
| 4,912,039 | 3/1990 | Riordan | 435/69.1 |

FOREIGN PATENT DOCUMENTS

174180  3/1986  European Pat. Off. .

OTHER PUBLICATIONS

Maniatis et al. (1982) *Molecular Cloning* (Cold Spring Harbor Laboratory, Cold Spring Harbor, NY) pp. 387-389.
Van der Bliek, A. M. et al. EMBO 5:3201-3208 (Dec. 1986).
Kennell, D. E. Progress in Nucleic Acid Research and Molecular Biology (Davidson, J. N. et al, ed.) Academic Press, NY 1971, pp. 259-261.
Meinkoth, J. et al. Anal. Biochem. 138:267-269.
de Bruijn, Mol. Cell. Biol., 6(12), 4714-4722 (1986).
Endicott et al., Mol. Cell. Biol., 7(11), 4075-4081 (1987).
Tsuruo et al., Gann, 74, 751-758 (1983).
Van der Bliek et al., Cancer Res., 48, 5927-5932 (1988).
van der Bliek et al., Gene, 71, 401-411 (1988).
Ng et al., Mol. Cell. Biol., 9(3), 1224-1232 (1989).
Akiyama et al., *Somat. Cell. Mol. Genet.*, 11, 117-126 (1985).
Aviv et al., *Proc. Natl. Acad. Sci. (USA)*, 69, 1408-1412 (1972).
Beck et al., Cancer Res., 39, 2070-2076 (1979).
Beck, *Advances in Enzyme Regulation*, 22, G. Weber, ed. (Pergamon Press Oxford, 1984) pp. 207-227.
Bell et al., *J. Clin. Oncol.*, 3, 311-315 (1985).
Benton et al., Science, 196, 180-182 (1977).
Biedler et al., Cancer Res., 30, 1174-1181 (1970).
Biedler et al. Cancer Treat. Rep., 67, 859-867 (1983).
Bitter et al. Gene, 32, 263-274 (1983).
Brahic et al. Proc. Natl. Acad. Sci. (USA), 75, 6125-6129 (1978).
Brown et al *Mol. Cell. Biol.*, 3, 1097-1107 (1983).
Cepko et al. Cell, 37, 1053-62 (1984).
Chirgwin et al. *Biochem.*, 18, 5294-5298 (1979).
Clark et al. *J. Cell. Biochem.*, 29, (suppl. 10A), 49, A130 (1986).
Cornwell et al. *J. Cell. Biochem.*, 29 (suppl. 10A), 50, A 131 (1986).

(List continued on next page.)

Primary Examiner—Margaret Moskowitz
Assistant Examiner—Ardin H. Marschel
Attorney, Agent, or Firm—Rothwell, Figg, Ernst & Kurz

[57] ABSTRACT

Genomic and cDNA clones of human genes which are selectively amplified or overexpressed in multidrug-resistant human tumor cells were isolated. Such clones may be used as probes in diagnostic tests to detect chemotherapy-resistant tumor cells and to predict tumor response to chemotherapy. The complete nucleotide sequence of the coding region of the human mdr1 gene and the complete corresponding amino acid sequence are disclosed.

8 Claims, 23 Drawing Sheets

OTHER PUBLICATIONS

Debenham et al. *Mol. Cell. Biol.*, 2, 881–889 (1982).
Eisenberg et al. *J. Mol. Biol.*, 179, 125–142 (1984).
Feinberg et al. *Analyt. Biochem.*, 132, 6–13 (1983).
Frei et al. *Proc. Natl. Acad. Sci. (USA)*, 81, 2873–2877 (1984).
Fojo et al. *Cancer Res.*, 45, 3002–3007 (1985).
Fojo et al. *Proc. Natl. Acad. Sci. (USA)*, 82 7661–7665 (1985).
Giles et al. *Nature*, 206, 93 (1965).
Gorman et al. *Mol. Cell. Biol.*, 2, 1044–1051 (1982).
Gros et al. *Proc. Natl. Acad. Sci. USA*, 83, 337–341 (1986).
Gros-Bellard et al. *Eur. J. Biochem.*, 36, 32–38 (1978).
Gros et al. *J. Cell. Biochem.*, 9C (suppl) 16, A1167 (1985).
Henikoff *Gene*, 28, 351–359 (1984).
Higgins et al. *EMBO J.*, 4, 1033–1040 (1985).
Kafatos et al. *Nucleic Acids Res.*, 7, 1541–1552 (1979).
Kartner et al. *Science*, 221, 1285–1288 (1983).
Kartner et al. *Nature*, 316, 820–823 (1985).
Kolata *Science*, 231, 220–221 (1986).
Leary et al. *Proc. Natl. Acad. Sci. (USA)*, 80, 4045–4049 (1983).
Lerner *Nature*, 299, 592–596 (1982).
Ling et al. *Cancer Treat. Rep.*, 67, 869–874 (1983).
Marglin et al. *Ann. Rev. Biochem.*, 39, 841–866 (1970).
Maxam et al. *Meth. Enzymol.* 65, 499–561 (1980).
McMaster et al. *Proc. Natl. Acad. Sci. (USA)*, 74, 4835 (1977).
Melton et al. *Nucleic Acids Res.*, 12, 7035–7056 (1984).
Messing *Meth. Enzymol.* 101, 20–78 (1983).
Niman et al. *Proc. Natl. Acad. Sci. (USA)*, 80, 4949–4953 (1983).
Pastan et al. *J. Cell. Biochem.*, 29 (suppl. 10A), 9, A13 (1986).
Ramu et al. *Cancer Treat. Rep.*, 67, 895–899 (1983).
Richert et al. *Proc. Natl. Acad. Sci. (USA)*, 82, 2330–2332 (1985).
Rigby et al. *Mol. Biol.*, 113, 237–251 (1977).
Rimm et al. *Gene*, 12, 301–309 (1980).
Riordan et al. *Nature*, 316, 817–819 (1985).
Robertson et al. *Mol. Cell., Biol.*, 4, 500–506 (1984).
Rogan et al. *Science*, 224, 994–996 (1984).
Roninson *Nucleic Acids Res.*, 11, 5413–5431 (1983).
Roninson et al. *Nature*, 309, 626–628 (1984).
Roninson et al. *J. Cell. Biochem.*, 29 (suppl. 10A), 12, A18 (1986).
Sanger et al. *Proc. Natl. Acad. Sci. USA*, 74, 5463–5467 (1977).
Shen et al. *Science*, 232, 643–645 (1986).
Southern *J. Mol. Biol.*, 98, 503–517 (1975).
Strauss et al. *Anal. Biochem.*, 154, 353–360 (1986).
Thomas *Proc. Natl. Acad., Sci. (USA)*, 77, 5201–5205 (1980).
Vieira et al. *Gene*, 19, 259–268 (1982).
Wolman et al. *Proc. Natl. Acad. Sci. (USA)*, 80, 807–809 (1983).
Yelton et al. *Ann. Rev. Biochem.*, 50, 657–680 (1981).
Young et al. *Proc. Natl. Acad. Sci. (USA)*, 80, 1194–1198 (1983).
Zagursky et al. *Gene Anal. Techn.*, 2, 89–94 (1985).

FIGURE 4

```
1    T GGA AGA CAA ATA CAC AAA ATT AGA AAA CAG TTT TTT CAT GCT
       Gly Arg Gln Ile His Lys Ile Arg Lys Gln Phe Phe His Ala

44   ATA ATG CGA CAG GAG ATA GGC TGG TTT GAT GTG CAC GAT GTT
     Ile Met Arg Gln Glu Ile Gly Trp Phe Asp Val His Asp Val

86   GGG GAG CTT AAC ACC CGA CTT ACA GA
     Gly Glu Leu Asn Thr Arg Leu Thr As

112                      GTAAGTATT TAGTTTTATG TTGAACTTGG GTGTCGTTCT
151  TATCCTTAGT AAAATGAAAT AGATGTCATC ACATCTGTTA GGAGGTGTTA
201  ATGTATCATT CAAAGGTACT TATGAGACAA AATTCCTTCT AAGCAGCAAC
251  AATGTCGTGT GCATCCTTTT GTTCCCAGTG CCTTGACAGG GTATGGGGGG
301  ACCTGCATGA CTAGCATTAA ATGAAGGACT GGGCTTTCCA GAATGAAGAA
351  ATCCTCTGAG AATGTGCAGT AGAGCAAAAC AAGATACTTT CTGAGGAAAT
401  TTCTGAGCAA TTTGAAATTC CTAGGTTGAA TACTTCTTGT GTACACGATG
```

FIGURE 4 (CONT'D)

```
451  TCCATTTCCT GGGGCCATGT GGCTATGGAT TTTTGTTGTT AATGACAAAT
501  ATCCTAGTAG AAACTTCTAC CCTGCTAAAT AAAACAAAGC ATAGGCACAA
551  AATACTCTAG CCATAAACTA CCCTACACTC AAAACAGGCT TCACGAGAAA
601  AGTTGATGTT TACAATTCTG ACAATTATTT CTAACACTAT CTGTTCTTTC
651  AG

653  T GAT GTC TCT AAG ATT AAT GAA GTT ATT GGT GAC AAA ATT GGA
     P Asp Val Ser Lys Ile Asn Glu Val Ile Gly Asp Lys Ile Gly

696  ATG TTC TTT CAG TCA ATG GCA ACA TTT TTC ACT GGG TTT ATA
     Met Phe Phe Gln Ser Met Ala Thr Phe Phe Thr Gly Phe Ile

738  GTA GGA TTT ACA CGT GGT TGG AAG CTA ACC CTT GTG ATT TTG
     Val Gly Phe Thr Arg Gly Trp Lys Leu Thr Leu Val Ile Leu

780  GCC ATC AGT CCT GTT CTT GGA CTG TCA G    807
     Ala Ile Ser Pro Val Leu Gly Leu Ser
```

FIGURE 5

```
  1  CCTACTCTAT TCAGATATTC TCCAGATTCC TAAAGATTAG AGATCATTTC
 51  TCATTCTCCT AGGAGTACTC ACTTCAGGAA GCAACCAGAT AAAAGAGAGG
101  TGCAACGGAA GCCAGAACAT TCCTCCTGGA AATTCAACCT GTTTCGCAGT
151  TTCTCGAGGA ATCAGCATTC AGTCAATCCG GGCCGGGGAGC AGTCATCTGT
201  GGTGAGGCTG ATTGGCTGGG CAGGAACAGC GCCGGGGGCGT GGGCTGAGCA
251  CAGGGCTTCG CTCTCTTTGC CACAGGAAGC CTGAGCTCAT TCGAGTAGCG
301  GCTCTTCCAA GCTCAAAGAA GCAGAGGCCG CTGTTCGTTT CCTTTAGGTC
351  TTTCCACTAA AGTCGGAGTA TCTTCTTCCA AGATTTCACG TCTTGGTGGC
401  CGTTCCAAGG AGCGCGAGGT CGGG
```

```
425  ATG GAT CTT GAA GGG GAC CGC AAT GGA GGA GCA AAG AAG AAG  466
     MET Asp Leu Glu Gly Asp Arg Asn Gly Gly Ala Lys Lys Lys

467  AAC TTT TTT AAA CTG AAC AAT AAA AGT GAA AAA GAT AAG AAG  508
     Asn Phe Phe Lys Leu Asn Asn Lys Ser Glu Lys Asp Lys Lys
```

FIGURE 5 (CONT'D)

```
509 GAA AAG AAA CCA ACT GTC AGT GTA TTT TCA ATG TTT CGC TAT  550
    GLU LYS LYS PRO THR VAL SER VAL PHE SER MET PHE ARG TYR

551 TCA AAT TGG CTT GAC AAG TTG TAT ATG GTG GTG GGA ACT TTG  592
    SER ASN TRP LEU ASP LYS LEU TYR MET VAL VAL GLY THR LEU

593 GCT GCC ATC ATC CAT GGG GCT GGA CTT CCT CTC ATG ATG CTG  634
    ALA ALA ILE ILE HIS GLY ALA GLY LEU PRO LEU MET MET LEU

635 GTG TTT GGA GAA ATG ACA GAT ATC TTT GCA AAT GCA GGA AAT  676
    VAL PHE GLY GLU MET THR ASP ILE PHE ALA ASN ALA GLY ASN

677 TTA GAA GAT CTG ATG TCA AAC ATC ACT AAT AGA AGT GAT ATC  718
    LEU GLU ASP LEU MET SER ASN ILE THR ASN ARG SER ASP ILE

719 AAT GAT ACA GGG TTC TTC ATG AAT CTG GAG GAA GAC ATG ACC  760
    ASN ASP THR GLY PHE PHE MET ASN LEU GLU GLU ASP MET THR
```

FIGURE 5 (CONT'D)

```
761 AGG TAT GCC TAT TAT TAC AGT GGA ATT GGT GCT GGG GTG CTG  802
    ARG TYR ALA TYR TYR TYR SER GLY ILE GLY ALA GLY VAL LEU

803 GTT GCT GCT TAC ATT CAG GTT TCA TTT TGG TGC CTG GCA GCT  844
    VAL ALA ALA TYR ILE GLN VAL SER PHE TRP CYS LEU ALA ALA

845 GGA AGA CAA ATA CAC AAA ATT AGA CAG AAA CAG TTT CAT GCT  886
    GLY ARG GLN ILE HIS LYS ILE ARG GLN LYS GLN PHE HIS ALA

887 ATA ATG CGA CAG GAG ATA GGC TGG TTT GAT GTG CAC GAT GTT  928
    ILE MET ARG GLN GLU ILE GLY TRP PHE ASP VAL HIS ASP VAL

929 GGG GAG CTT AAC ACC CGA CTT ACA GAT GAT GTC TCT AAG ATT  970
    GLY GLU LEU ASN THR ARG LEU THR ASP ASP VAL SER LYS ILE
```

FIGURE 5 (CONT'D)

```
 971 AAT GAA GTT ATT GGT GAC AAA ATT GGA ATG TTC TTT CAG TCA 1012
     Asn Glu Val Ile Gly Asp Lys Ile Gly Met Phe Phe Gln Ser

1013 ATG GCA ACA TTT TTC ACT GGG TTT ATA GTA GGA TTT ACA CGT 1054
     Met Ala Thr Phe Phe Thr Gly Phe Ile Val Gly Phe Thr Arg

1055 GGT TGG AAG CTA ACC CTT GTG ATT TTG GCC ATC AGT CCT GTT 1096
     Gly Trp Lys Leu Thr Leu Val Ile Leu Ala Ile Ser Pro Val

1097 CTT GGA CTG TCA GCT GCT GTC TGG GCA AAG ATA CTA TCT TCA 1138
     Leu Gly Leu Ser Ala Ala Val Trp Ala Lys Ile Leu Ser Ser

1139 TTT ACT GAT AAA GAA CTC TTA GCG TAT GCA AAA GCT GGA GCA 1180
     Phe Thr Asp Lys Glu Leu Leu Ala Tyr Ala Lys Ala Gly Ala
```

FIGURE 5 (CONT'D)

```
1181 GTA GCT GAA GAG GTC TTG GCA GCA ATT AGA ACT GTG ATT GCA  1222
     Val Ala Glu Glu Val Leu Ala Ala Ile Arg Thr Val Ile Ala

1223 TTT GGA GGA CAA AAG AAA GAA CTT GAA AGG TAC AAC AAA AAT  1264
     Phe Gly Gly Gln Lys Lys Glu Leu Glu Arg Tyr Asn Lys Asn

1265 TTA GAA GAA GCT AAA AGA ATT GGG ATA AAG AAA GCT ATT ACA  1306
     Leu Glu Glu Ala Lys Arg Ile Gly Ile Lys Lys Ala Ile Thr

1307 GCC AAT ATT TCT ATA GGT GCT GCT TTC CTG ATC CTG TAT GCA  1348
     Ala Asn Ile Ser Ile Gly Ala Ala Phe Leu Ile Leu Tyr Ala

1349 TCT TAT GCT CTG GCC TTC TGG TAT GGG ACC ACC TTG GTC CTC  1390
     Ser Tyr Ala Leu Ala Phe Trp Tyr Gly Thr Thr Leu Val Leu
```

FIGURE 5 (CONT'D)

```
1391 TCA GGG GAA TAT TCT ATT GGA CAA GTA CTC ACT GTA TTC TTT 1432
     Ser Gly Glu Tyr Ser Ile Gly Gln Val Leu Thr Val Phe Phe

1433 TCT GTA TTA ATT GGG GCT TTT AGT GTT GGA CAG GCA TCT CCA 1474
     Ser Val Leu Ile Gly Ala Phe Ser Val Gly Gln Ala Ser Pro

1475 AGC ATT GAA GCA TTT GCA AAT GCA AGA GGA GCA GCT TAT GAA 1516
     Ser Ile Glu Ala Phe Ala Asn Ala Arg Gly Ala Ala Tyr Glu

1517 ATC TTC AAG ATA ATT GAT AAT AAG CCA AGT ATT GAC AGC TAT 1558
     Ile Phe Lys Ile Ile Asp Asn Lys Pro Ser Ile Asp Ser Tyr

1559 TCG AAG AGT GGG CAC AAA CCA GAT AAT ATT AAG GGA AAT TTG 1600
     Ser Lys Ser Gly His Lys Pro Asp Asn Ile Lys Gly Asn Leu
```

FIGURE 5 (CONT'D)

```
1601 GAA TTC AGA AAT GTT CAC TTC AGT TAC CCA TCT CGA AAA GAA  1642
     Glu Phe Arg Asn Val His Phe Ser Tyr Pro Ser Arg Lys Glu

1643 GTT AAG ATC TTG AAG GGC CTG AAC CTG AAG GTG CAG AGT GGG  1684
     Val Lys Ile Leu Lys Gly Leu Asn Leu Lys Val Gln Ser Gly

1685 CAG ACG GTG GCC CTG GTT GGA AAC AGT GGC TGT GGG AAG AGC  1726
     Gln Thr Val Ala Leu Val Gly Asn Ser Gly Cys Gly Lys Ser

1727 ACA ACA GTC CAG CTG ATG CAG AGG CTC TAT GAC CCC ACA GAG  1768
     Thr Thr Val Gln Leu Met Gln Arg Leu Tyr Asp Pro Thr Glu

1769 GGG ATG GTC AGT GTT GAT GGA CAG GAT ATT AGG ACC ATA AAT  1810
     Gly Met Val Ser Val Asp Gly Gln Asp Ile Arg Thr Ile Asn
```

FIGURE 5 (CONT'D)

```
1811 GTA AGG TTT CTA CGG GAA ATC ATT GGT GTG GTG AGT CAG GAA  1852
     Val Arg Phe Leu Arg Glu Ile Ile Gly Val Val Ser Gln Glu

1853 CCT GTA TTG TTT GCC ACC ACG ATA GCT GAA AAC ATT CGC TAT  1894
     Pro Val Leu Phe Ala Thr Thr Ile Ala Glu Asn Ile Arg Tyr

1895 GGC CGT GAA AAT GTC ACC ATG GAT GAG ATT GAG AAA GCT GTC  1936
     Gly Arg Glu Asn Val Thr Met Asp Glu Ile Glu Lys Ala Val

1937 AAG GAA GCC AAT GCC TAT GAC TTT ATC ATG AAA CTG CCT CAT  1978
     Lys Glu Ala Asn Ala Tyr Asp Phe Ile Met Lys Leu Pro His

1979 AAA TTT GAC ACC CTG GTT GGA GAG AGA GGG GCC CAG TTG AGT  2020
     Lys Phe Asp Thr Leu Val Gly Glu Arg Gly Ala Gln Leu Ser

2021 GGT GGG CAG AAG CAG AGG ATC GCC ATT GCA CGT GCC CTG GTT  2062
     Gly Gly Gln Lys Gln Arg Ile Ala Ile Ala Arg Ala Leu Val
```

FIGURE 5 (CONT'D)

```
2063 CGC AAC CCC AAG ATC CTC CTG CTG GAT GAG GCC ACG TCA GCC 2104
     Arg Asn Pro Lys Ile Leu Leu Leu Asp Glu Ala Thr Ser Ala

2105 TTG GAC ACA GAA AGC GAA GCA GTG GTT CAG GTG GCT CTG GAT 2146
     Leu Asp Thr Glu Ser Glu Ala Val Val Gln Val Ala Leu Asp

2147 AAG GCC AGA AAA GGT CGG ACC ATT GTG ATA GCT CAT CGT 2188
     Lys Ala Arg Lys Gly Arg Thr Thr Ile Val Ile Ala His Arg

2189 TTG TCT ACA GTT CGT AAT GCT GAC GTC ATC GCT GGT TTC GAT 2230
     Leu Ser Thr Val Arg Asn Ala Asp Val Ile Ala Gly Phe Asp

2231 GAT GGA GTC ATT GTG GAG AAA GGA AAT CAT GAT GAA CTC ATG 2272
     Asp Gly Val Ile Val Glu Lys Gly Asn His Asp Glu Leu Met

2273 AAA GAG AAA GGC ATT TAC TTC AAA CTT GTC ACA ATG CAG ACA 2314
     Lys Glu Lys Gly Ile Tyr Phe Lys Leu Val Thr Met Gln Thr
```

FIGURE 5 (CONT'D)

```
2315 GCA GGA AAT GAA GTT GAA TTA GAA AAT GCA GCT GAT GAA TCC 2356
     ALA GLY ASN GLU VAL GLU LEU GLU ASN ALA ALA ASP GLU SER

2357 AAA AGT GAA ATT GAT GCC TTG GAA ATG TCT TCA AAT GAT TCA 2398
     LYS SER GLU ILE ASP ALA LEU GLU MET SER SER ASN ASP SER

2399 AGA TCC AGT CTA ATA AGA AAA AGA TCA ACT CGT AGG AGT GTC 2440
     ARG SER SER LEU ILE ARG LYS ARG SER THR ARG ARG SER VAL

2441 CGT GGA TCA CAA GCC CAA GAC AGA AAG CTT AGT ACC AAA GAG 2482
     ARG GLY SER GLN ALA GLN ASP ARG LYS LEU SER THR LYS GLU

2483 GCT CTG GAT GAA AGT ATA CCT CCA GTT TCC TTT TGG AGG ATT 2524
     ALA LEU ASP GLU SER ILE PRO PRO VAL SER PHE TRP ARG ILE

2525 ATG AAG CTA AAT TTA ACT GAA TGG CCT TAT TTT GTT GTT GGT 2566
     MET LYS LEU ASN LEU THR GLU TRP PRO TYR PHE VAL VAL GLY
```

FIGURE 5 (CONT'D)

```
2567 GTA TTT TGT GCC ATT ATA AAT GGA GGC CTG CAA CCA GCA TTT  2608
     Val Phe Cys Ala Ile Ile Asn Gly Gly Leu Gln Pro Ala Phe

2609 GCA ATA ATA TTT TCA AAG ATT ATA GGG GTT TTT ACA AGA ATT  2650
     Ala Ile Ile Phe Ser Lys Ile Ile Gly Val Phe Thr Arg Ile

2651 GAT GAT CCT GAA ACA AAA CGA CAG AAT AGT AAC TTG TTT TCA  2692
     Asp Asp Pro Glu Thr Lys Arg Gln Asn Ser Asn Leu Phe Ser

2693 CTA TTG TTT CTA GCC CTT GGA ATT ATT TCT TTT ATT ACA TTT  2734
     Leu Leu Phe Leu Ala Leu Gly Ile Ile Ser Phe Ile Thr Phe

2735 TTC CTT CAG GGT TTC ACA TTT GGC AAA GCT GGA GAG ATC CTC  2776
     Phe Leu Gln Gly Phe Thr Phe Gly Lys Ala Gly Glu Ile Leu

2777 ACC AAG CGG CTC CGA TAC ATG GTT TTC CGA TCC ATG CTC AGA  2818
     Thr Lys Arg Leu Arg Tyr Met Val Phe Arg Ser Met Leu Arg
```

FIGURE 5 (CONT'D)

```
2819 CAG GAT GTG AGT TGG TTT GAT GAC CCT AAA AAC ACC ACT GGA  2860
     GLN ASP VAL SER TRP PHE ASP ASP PRO LYS ASN THR THR GLY

2861 GCA TTG ACT ACC AGG CTC GCC AAT GAT GCT GCT CAA GTT AAA  2902
     ALA LEU THR THR ARG LEU ALA ASN ASP ALA ALA GLN VAL LYS

2903 GGG GCT ATA GGT TCC AGG CTT GCT GTA ATT ACC CAG AAT ATA  2944
     GLY ALA ILE GLY SER ARG LEU ALA VAL ILE THR GLN ASN ILE

2945 GCA AAT CTT GGG ACA GGA ATA ATT ATA TCC TTC ATC TAT GGT  2986
     ALA ASN LEU GLY THR GLY ILE ILE ILE SER PHE ILE TYR GLY

2987 TGG CAA CTA ACA CTG TTA CTC TTA GCA ATT GTA CCC ATC ATT  3028
     TRP GLN LEU THR LEU LEU LEU LEU ALA ILE VAL PRO ILE ILE

3029 GCA ATA GCA GGA GTT GTT GAA ATG AAA ATG TTG TCT GGA CAA  3070
     ALA ILE ALA GLY VAL VAL GLU MET LYS MET LEU SER GLY GLN
```

FIGURE 5 (CONT'D)

```
3071 GCA CTG AAA GAT AAG AAA GAA CTA GAA GGT GCT GGG AAG ATC  3112
     Ala Leu Lys Asp Lys Lys Glu Leu Glu Gly Ala Gly Lys Ile

3113 GCT ACT GAA GCA ATA GAA AAC TTC CGA ACC GTT GTT TCT TTG  3154
     Ala Thr Glu Ala Ile Glu Asn Phe Arg Thr Val Val Ser Leu

3155 ACT CAG GAG CAG AAG TTT GAA CAT ATG TAT GCT CAG AGT TTG  3196
     Thr Gln Glu Gln Lys Phe Glu His Met Tyr Ala Gln Ser Leu

3197 CAG GTA CCA TAC AGA AAC TCT TTG AGG AAA GCA CAC ATC TTT  3238
     Gln Val Pro Tyr Arg Asn Ser Leu Arg Lys Ala His Ile Phe

3239 GGA ATT ACA TTT TCC TTC ACC CAG GCA ATG ATG TAT TTT TCC  3280
     Gly Ile Thr Phe Ser Phe Thr Gln Ala Met Met Tyr Phe Ser

3281 TAT GCT GGA TGT TTC CGG TTT GGA GCC TAC TTG GTG GCA CAT  3322
     Tyr Ala Gly Cys Phe Arg Phe Gly Ala Tyr Leu Val Ala His
```

FIGURE 5 (CONT'D)

```
3323 AAA CTC ATG AGC TTT GAG GAT GTT CTG TTA GTA TTT TCA GCT  3364
     LYS LEU MET SER PHE GLU ASP VAL LEU LEU VAL PHE SER ALA

3365 GTT GTC TTT GGT GCC ATG GCC GTG GGG CAA GTC AGT TCA TTT  3406
     VAL VAL PHE GLY ALA MET ALA VAL GLY GLN VAL SER SER PHE

3407 GCT CCT GAC TAT GCC AAA ATA TCA GCA GCC CAC ATC          3448
     ALA PRO ASP TYR ALA LYS ILE SER ALA ALA HIS ILE

3449 ATC ATG ATC ATT GAA AAA ACC CCT TTG ATT GAC AGC TAC AGC  3490
     ILE MET ILE ILE GLU LYS THR PRO LEU ILE ASP SER TYR SER

3491 ACG GAA GGC CTA ATG CCG AAC ACA TTG GAA GGA AAT GTC ACA  3532
     THR GLU GLY LEU MET PRO ASN THR LEU GLU GLY ASN VAL THR

3533 TTT GGT GAA GTT GTA TTC AAC TAT CCC ACC CGA CCG GAC ATC  3574
     PHE GLY GLU VAL VAL PHE ASN TYR PRO THR ARG PRO ASP ILE
```

FIGURE 5 (CONT'D)

```
3575 CCA GTG CTT CAG GGA CTG AGC CTG GAG GTG AAG AAG GGC CAG  3616
     Pro Val Leu Gln Gly Leu Ser Leu Glu Val Lys Lys Gly Gln

3617 ACG CTG GCT CTG GTG GGC AGC AGT GGC AGT TGT GGG AAG AGC ACA  3658
     Thr Leu Ala Leu Val Gly Ser Ser Gly Cys Gly Lys Ser Thr

3659 GTG GTC CAG CTC CTG GAG CGG TTC TAC GAC CCC TTG GCA GGG  3700
     Val Val Gln Leu Leu Glu Arg Phe Tyr Asp Pro Leu Ala Gly

3701 AAA GTG CTG CTT GAT GGC AAA GAA ATA AAG CGA CTG AAT GTT  3742
     Lys Val Leu Leu Asp Gly Lys Glu Ile Lys Arg Leu Asn Val

3743 CAG TGG CTC CGA GCA CAC CTG GGC ATC GTG TCC CAG GAG CCC  3784
     Gln Trp Leu Arg Ala His Leu Gly Ile Val Ser Gln Glu Pro

3785 ATC CTG TTT GAC TGC AGC ATT GCT GAG AAC ATT GCC TAT GGA  3826
     Ile Leu Phe Asp Cys Ser Ile Ala Glu Asn Ile Ala Tyr Gly
```

FIGURE 5 (CONT'D)

```
3827 GAC AAC AGC CGG GTG GTG TCA CAG GAA GAG ATC GTG AGG GCA   3868
     Asp Asn Ser Arg Val Val Ser Gln Glu Glu Ile Val Arg Ala

3869 GCA AAG GAG AAC ATA CAT GCC TTC ATC GAG TCA CTG CCT        3910
     Ala Lys Glu Asn Ile His Ala Phe Ile Glu Ser Leu Pro

3911 AAT AAA TAT AGC ACT AAA GTA GGA GAC AAA GGA ACT CAG CTC   3952
     Asn Lys Tyr Ser Thr Lys Val Gly Asp Lys Gly Thr Gln Leu

3953 TCT GGT GGC CAG AAA CAA CGC ATT GCC ATA GCT CGT GCC CTT   3994
     Ser Gly Gly Gln Lys Gln Arg Ile Ala Ile Ala Arg Ala Leu

3995 GTT AGA CAG CCT CAT ATT TTG CTT TTG GAT GAA GCC ACG TCA   4036
     Val Arg Gln Pro His Ile Leu Leu Leu Asp Glu Ala Thr Ser

4037 GCT CTG GAT ACA GAA AGT GAA AAG GTT GTC CAA GAA GCC CTG   4078
     Ala Leu Asp Thr Glu Ser Glu Lys Val Val Gln Glu Ala Leu
```

FIGURE 5 (CONT'D)

```
4079 GAC AAA GCC AGA GAA GGC CGC ACC TGC ATT GTG ATT GCT CAC  4120
     Asp Lys Ala Arg Glu Gly Arg Thr Cys Ile Val Ile Ala His

4121 CGC CTG TCC ACC ATC CAG AAT GCA GAC TTA ATA GTG GTG TTT  4162
     Arg Leu Ser Thr Ile Gln Asn Ala Asp Leu Ile Val Val Phe

4163 CAG AAT GGC AGA GTC AAG GAG CAT CAG ACG CAT CAG CAG CTG  4204
     Gln Asn Gly Arg Val Lys Glu His Gln Thr His Gln Gln Leu

4205 CTG GCA CAG AAA GGC ATC TAT TTT TCA ATG GTC AGT GTC CAG  4246
     Leu Ala Gln Lys Gly Ile Tyr Phe Ser Met Val Ser Val Gln

4247 GCT GGA ACA AAG CGC CAG TGA  4267
     Ala Gly Thr Lys Arg Gln Ter
```

FIGURE 5 (CONT'D)

```
4268  ACTCTGACTG TATGAGATGT TAAATACTTT TTAATATTTG TTTAGATATG
4318  ACATTATTC AAAGTTAAAA GCAAACACTT ACAGAATTAT GAAGAGGTAT
4368  CTGTTTAACA TTTCCTCAGT CAAGTTCAGA GTCTTCAGAG ACTTCGTAAT
4418  TAAAGGAACA GAGTGAGAGA CATCATCAAG TGGAGAGAAA TCATAGTTTA
4468  AACTGCATTA TAAATTTTAT AACAGAATTA AAGTAGATTT TAAAAGATAA
4518  AATGTGTAAT TTTGTTTATA TTTTCCCATT TGGACTGTAA CTGACTGCCT
4568  TGCTAAAAGA TTATAGAAGT AGCAAAAAGT ATTGAAATGT TTGCATAAAG
4618  TGTCTATAAT AAAACTAAAC TTTCATGTGA AAAAAAAAAA AAAAAAAAAA
4668  AA
``` ized with 5,206,352

COMPOSITIONS FOR CLONES CONTAINING DNA SEQUENCES ASSOCIATED WITH MULTIDRUG RESISTANCE IN HUMAN CELLS

This is a continuation of U.S. Ser. No. 06/892,575, filed Aug. 1, 1986, which is a continuation-in-part of U.S. Ser. No. 06/845,610, filed Mar. 28, 1986, both abandoned.

Background

The present invention pertains in general to diagnostic materials and methods and in particular to materials and methods for the detection of multidrug-resistant tumor cells.

Selection of mammalian cells for resistance to plant alkaloids or antitumor antibiotics frequently results in the development of cross-resistance to other drugs unrelated in their structure and mode of action to the original selective agent. Biedler et al., *Cancer Res.*, 30, 1174 (1970). The phenomenon of multidrug resistance constitutes a major problem in cancer chemotherapy since it involves resistance to some of the most commonly used anticancer drugs.

Multidrug resistance in most cases appears to result from decreased intracellular drug accumulation, probably as a result of alterations in the plasma membrane. Biedler et al., *Cancer Treat. Rep.*, 67, 859 (1983); Ling et al., *Cancer Treat. Rep.*, 67, 869 (1983); Ramu et al., *Cancer Treat. Rep.*, 67, 895 (1983); and Beck et al., *Cancer Res.*, 39, 2070 (1979).

In some hamster, mouse and human multidrug-resistant cell lines, resistance correlates with over expression of a 170,000 m.w. membrane glycoprotein (P-glycoprotein) or a 19,000 m.w. cytosolic protein. Kartner et al., *Science*, 221, 1285–1288 (1983); Biedler et al., *Cancer Treat. Rep.*, 67, 859 (1983). Immunoblotting techniques applied to cells from human cancer patients reveal high levels of P-glycoprotein in some cases of advanced, nonresponsive ovarian cancer. Bell et al., *J. Clin. Oncol.*, 3, 311–315 (1985).

P-glycoprotein-specific, monoclonal antibodies raised against multidrug-resistant Chinese hamster ovary (CHO) cell lines and cross reactive with human cell lines apparently bind to multidrug-resistant mammalian cells to a degree correlated with the degree of their drug resistance. Kartner et al., *Nature*, 316, 820–823 (1985). These monoclonals may all bind to a C-terminal intracellular region of a proposed P-glycoprotein polypeptide. Kartner et al., *Nature*, 316, 820–823 (1985). P-glycoprotein specific cDNA clones have been isolated from Chinese hamster ovary cells, and these clones revealed amplification of the P-glycoprotein gene in multidrug resistant hamster, mouse and human cells when employed in a Southern blotting procedure. Riordan et al., *Nature*, 316, 817–819 (1985). However, Riordan et al. provides no indication whether the hamster P-glycoprotein cDNA clones may be used to detect the expression of human P-glycoprotein genes at the level of RNA.

In a different approach to the examination of multidrug-resistance, a common region of DNA is found to be amplified in two different multidrug-resistant Chinese hamster cell lines selected for resistance to either colchicine or Adriamycin. Roninson et al., *Nature*, 309, 626 (1984). This region was found to contain a transcription unit, presently designated mdr. Expression of the mdr mRNA correlates with multidrug resistance in the hamster cells. Gros et al., *J. Cell. Biochem.*, 9C (suppl.), 16, A1167 (1985); and Gros et al., *Proc. Natl. Acad. Sci. (USA)*, 83, 337 (1986). However, probes derived from the hamster mdr gene are not useful probes for human cells inasmuch as, even though these probes hybridize to human DNA (as illustrated in Example 2, infra), they do not hybridize efficiently with human mdr mRNA, despite the impression given in a report on a workshop dealing with multidrug resistance [Kolata, *Science*, 231, 220–221 (1986)].

Therefore, in the absence of a probe for human mdr gene expression, there is a need for a reliable method for detecting the presence of multidrug-resistant cells in a human tumor either prior to or during chemotherapy.

SUMMARY OF THE INVENTION

The present invention provides an isolated nucleic acid sequence for a human mdr gene associated with multidrug resistance in human cells.

A presently-preferred embodiment of the present invention provides an isolated and purified nucleic acid selected from the group consisting of: (a) a nucleic acid comprising a member of the group consisting of a continuous sequence of nucleotides as set forth in FIG. 4, in FIG. 5, in pHDR4.4 (ATCC 40227), in pHDR4.5 (ATCC 40228), in pHDR5A (ATCC 67040), in pHDR5B (ATCC 67041), in pHDR10 (ATCC 67042) and in pHDR104 (ATCC 67156); (b) a nucleic acid comprising a nucleotide sequence which hybridizes with at least one of the continuous sequences of nucleotides as set forth in (a) or which is contained within the same mRNA molecule of human origin or cDNA molecule of human origin as at least one of the continuous sequences of nucleotides as set forth in (a); (c) nucleic acids comprising a nucleotide sequence which hybridizes with any nucleotide sequences described in (b); and (d) nucleic acids comprising a sequence of nucleotides which, but for the degeneracy of the genetic code, would hybridize with at least one of the continuous sequences of nucleotides as set forth in (a), (b), or (c). Standard conditions for identifying the presence or absence of "hybridization" herein are reactions conducted in 4 X SSC and 0.5% SDS at a temperature of 65 degrees C. in the last wash. A nucleic acid probe according to the preferred embodiment may also include a label associated with one of these nucleic acids. Polypeptides encoded by these nucleic acids may be expressed or synthesized chemically, and used, in conjunction with diluents, adjuvants, or carriers of the sort well known to those skilled in the art, to raise monoclonal or polyclonal antibodies or to elicit immune response in patients. Such antibodies may be utilized as a diagnostic reagent using various presently available immunodiagnostic techniques, or employed as immunotherapeutic agents.

BRIEF DESCRIPTION OF THE DRAWINGS

FIG. 4 shows the nucleic acid sequence of the pMDR1 clone and the amino acid sequence encoded by exons 1 to 111, inclusive, and 653 to 807, inclusive.

FIG. 5 shows the human mdr1 cDNA sequence from overlapping clones pHDR10, pHDR5 and pHDR104 and the amino acid sequence encoded by exon 425 to 4267, inclusive.

DETAILED DESCRIPTION

Figure 1:
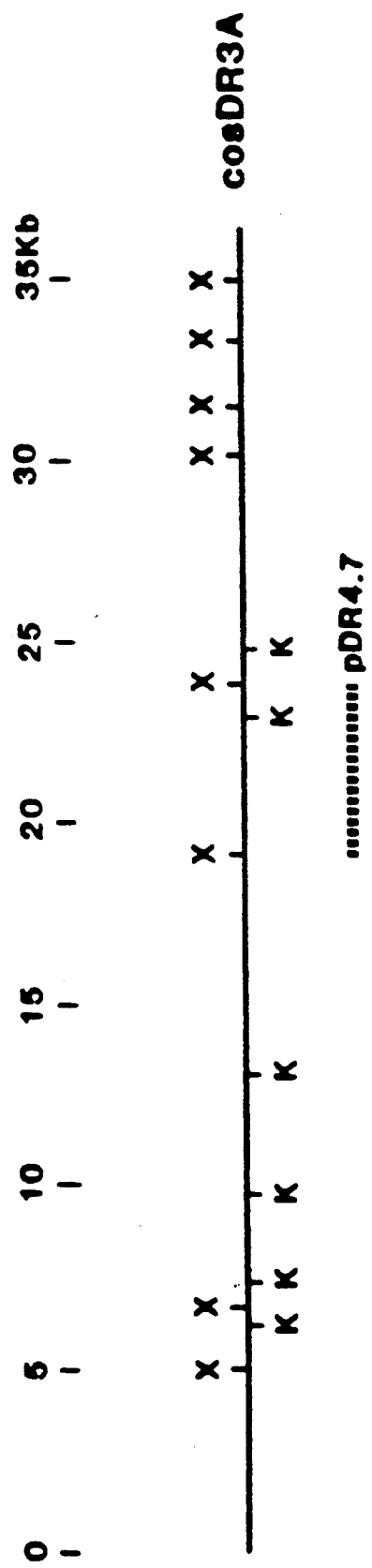
FIG. 1 is a partial restriction map of the cosmid clone cosDR3A which contains a 5' portion of the transcribed mdr region isolated from Chinese hamster cells.

Preliminary announcements of the obtaining of mdr1 clones according to the present invention and of uses therefor have been made by the inventors at the *UCLA Symposia on Molecular and Cellular Biology*, Jan. 20—Feb. 15, 1986. Roninson et al., *J. Cell. Biochem.*, 29 (suppl. 10A), 12, A18 (1986); Pastan et al., *J. Cell. Biochem.*, 29 (suppl. 10A), 9, A13 (1986); Clark et al., *J. Cell. Biochem.*, 29 (suppl. 10A), 49, A130 (1986); and Cornwell et al., J. Cell. Biochem., 29 (suppl. 10A), 50, A131 (1986).

A recently published European Patent Application No. 174,810 by John R. Riordan, entitled "Multidrug Resistance in Mammalian Cell Lines And Isolation Of Determinant Glycoprotein DNA," describes isolation of Chinese hamster cDNA clones specific for P-glycoprotein, and it suggests using P-glycoprotein-specific cDNA as a probe in determining multidrug resistance in cells. Although only Southern blot hybridization between hamster cDNA and human genomic DNA is described, claim 18 of Riordan, EPA 174,810, relates to a P-glycoprotein-specific DNA molecule "derived from a source selected from the group consisting of Chinese Hamster Ovary cells, mouse cells and human cells." In the event that the mdr clones described herein represent the human P-glycoprotein gene sequences, which is likely to be the case as discussed in Example 10 below, it should be noted that Riordan, EPA 174,810, does not disclose a human mdr gene or any portion thereof.

In fact, Riordan, EPA 174,810, post-dates the publication of Roninson et al., *Nature*, 309, 626 (1984) which described cloning of a segment of the Chinese hamster mdr region. The work describe in Roninson et al., *Nature*, 309, was followed by isolation of the entire Chinese hamster mdr gene [Gros et al., *J. Cell. Biochem.* and *Proc. Nat'l. Acad. Sci. (USA)*, supra] as opposed to only partial cDNA clones of the Chinese hamster P-glycoprotein genes, as described in Riordan, EPA 174,810. Riordan, EPA 174,810, provides no evidence for the ability of Chinese hamster clones to detect the expression of human P-glycoprotein mRNA. Furthermore, the use of P-glycoprotein cDNA as a probe for detection of multidrug resistance in tumor cells is described in Riordan, EPA 174,180, only in terms of detection of amplified P-glycoprotein genes but not in terms of detection of increased P-glycoprotein mRNA expression. Increased mRNA expression, as described in Example 7 below, provides a much more useful diagnostic marker for multidrug resistance than does gene amplification. In addition, although claiming P-glycoprotein cDNA sequences of human origin, Riordan, EPA 174,810, contains no indication as to how such sequences would be obtained, e.g. the source of human DNA or RNA, or stringency conditions for screening of human cDNA or genomic libraries with a Chinese hamster probe. As shown in Example 2 below, there is a low level of homology between the hamster and human mdr genes, at least within the 5' half of the gene, which presents a considerable technical problem in the isolation of human mdr DNA sequences.

In the following examples, nucleic acid clones for human mdr genes and uses for the nucleotide sequences of mdr clones are described. In Example 1 a Chinese hamster mdr clone is used to identify sequences hybridizing with human DNA. Example 2 describes the identification and isolation of DNA sequences comprising human mdr genes. In Example 3, amplification of mdr genes in human drug-resistant cells is demonstrated. A characterization of clones containing mdr sequences is presented in Example 4. In Example 5, DNA rearrangement involving mdr genes is examined. In Example 6, transcription of the mdr1 gene in human cells is demonstrated. Example 7 describes an investigation into expression levels of the mdr1 sequence during the course of development of multidrug resistance in human cells. In Example 8, expression of mdr genes out of proportion to gene amplification is demonstrated. Example 9 provides a description of a genomic clone containing a segment of the mdr1 gene. In Example 10, cDNA clones of the mdr1 gene and the cDNA sequence of the human mdr1 gene is disclosed are described. In Example 11, diagnostic and therapeutic procedures using probes according to the present invention are described.

EXAMPLE 1

Derivation and characterization of multidrug-resistant sublines of human KB cells are described elsewhere. Akiyama et al., *Somat. Cell Mol. Genet.*, 11, 117 (1985); Fojo et al., *Cancer Res.*, 45, 3002 (1985); and Richert et al., *Proc. Natl. Acad. Sci. (USA)*, 82, 2330 (1985). The multi-drug resistant phenotype is unstable in the most highly resistant lines, with a decrease in resistance when grown in the absence of the drugs. Using the in-gel DNA renaturation technique [according to Roninson, *Nucleic Acids Res.*, 11, 5413 (1983)], several of the multidrug-resistant sublines of KB cells are known to contain amplified DNA sequences, and karyotypic analysis reveal double minute chromosomes in these cells. Fojo et al., *Proc. Natl. Acad. Sci. (USA)*, 82, 7661 (1985).

Sublines of the human KB carcinoma cells, selected for resistance to colchicine, vinblastine or Adriamycin [Akiyama et al., supra; Fojo et al., Cancer Res. supra; Richert et al., supra and Shen et al., *Science*, 232, 643–645 (1986)], demonstrate the multidrug-resistant phenotype. Several of these sublines are described in Table 1. Fojo et al., *Proc. Natl. Acad. Sci. USA*, 82, 7661 (1985). In Table 1, "n/d" means not determined. KB-8-5-11, KB-8-511-24, KB-C3 and KB-C4 cell lines are subclones selected in 100 ng/ml, 1 μg/ml, 3 μg/ml and 4 μg/ml Adriamycin, respectively. Relative resistance is expressed as the $D_{10}$ of the resistant cell line divided by the $D_{10}$ of the parental DB-3-1 cells. Akiyama et al., supra.

TABLE 1

| Cell Line | Relative Resistance To: | | |
|---|---|---|---|
| | Colchicine | Adriamycin | Vinblastine |
| KB-3-1 | 1 | 1 | 1 |
| KB-8-5-11 | 40 | 23 | 51 |
| KB-8-5-11-24 | 128 | 26 | 20 |
| KB-C3 | 487 | 141 | 206 |
| KB-C4 | 1750 | 254 | 159 |
| KB-C1-R1 | 6 | 3 | 4 |
| KB-V1 | 171 | 422 | 213 |
| KB-A1 | 19 | 97 | 43 |
| KB-A2 | n/d | 140 | n/d |

These multidrug-resistant human KB cell lines were used to determine whether DNA sequences homologous to the hamster mdr gene are present in the human genome. The Chinese hamster mdr DNA sequences used in this study were derived from the cosmid clone cosDR3A, containing a 5' segment of the hamster mdr gene. After digestion with the restriction enzymes XbaI and KpnI, individual 1.5-6 kilobase (kb) restriction fragments from this cosmid were either subcloned into pSP65 plasmid vector commercially available from Promega Biotec, Madison, Wis., or gel-purified prior to labeling with $^{32}$P. A vector including a 4.7 kb XbaI fragment, designated pDR4.7, contained DNA sequences hybridizing to human DNA.

In FIG. 1, a partial restriction endonuclease map of the cosmid clone cosDR3A, containing a 5' portion of the transcribed mdr region amplified in multidrug-resistant Chinese hamster cells, is presented along with a dashed line aligned to indicate the portion of ROS DR3A which hybridizes to pDR4.7. In FIG. 1, X denotes an XbaI site and K identifies a KpnI site. Cloning and characterization of this region are described in Gros et al., *Proc. Natl. Acad. Sci. USA*, 83, 337 (1986).

EXAMPLE 2

In order to identify and isolate segments of DNA comprising the human mdr genes, individual 1.5–6 kilobase (kb) size fragments of the cloned hamster mdr gene were isolated as a series of recombinant subclones in a pSP64 plasmid vector commercially available from Promega Biotec and described in Promega Biotec Technical Bulletin No. 13 as well as in Melton, *Nucleic Acids Res.*, 12, 7055-7056 (1984). Individual subclones were then labeled with $^{32}$P and were used as probes for Southern blot hybridization with human DNA digested with restriction enzymes.

The subclones were then used as probes for hybridization with restriction digests of human genomic DNA. Most probes, when used under conditions of low hybridization stringency, produced either no hybridization signal or a continuous smear suggesting cross-hybridization with human repetitive DNA sequences. However, one of the subclones, designated pDR4.7 and illustrated in FIG. 1, gave rise to distinct bands when hybridized to human DNA under low stringency conditions.

Inasmuch as subclone pDR4.7, produced a distinct hybridization signal, this subclone contained hamster DNA sequences homologous to the human mdr genes. pDR4.7 hybridized to two major different EcoRI restriction fragments in human DNA, although in some experiments as many as nine additional EcoRI fragments could be detected.

EXAMPLE 3

In order to determine whether an mdr gene is amplified in multidrug-resistant human cells, DNA extracted from the parental KB-3-1 cells and various multidrug-resistant sublines described in Table 1 by the procedure of Gros-Bellard et al., *Eur. J. Biochem.*, 36, 32 (1978) was digested with EcoRI or HindIII, electrophoresed on agarose gels and hybridized to the pDR4.7 probe by the procedure of Southern [Southern, *J. Mol. Biol.*, 98, 503, (1975)].

In the Southern hybridization of pDR4.7 with EcoRI-digested DNA from multidrug-resistant KB cells, DNA was extracted as previously described [Gros-Bellard et al., *Eur. J. Biochem.*, 36, 32 (1978)]. The concentration of EcoRI-digested DNA was determined by the diphenylamine reaction [Giles et al., *Nature*, 206, 93 (1965)] and 5 μg of DNA were loaded onto each lane. After electrophoresis, DNA was transferred onto a nylon (Biodyne) membrane [Southern, supra]. Plasmid pDR4.7 was digested with XbaI, the insert was gel-purified and labeled with $^{32}$P to a specific activity of $3 \times 10^9$ dpm/μg by oligolabeling [Feinberg et al., *Analyt. Biochem.*, 132, 6 (1983)]. Hybridization was done at 65° C. in 5×SSPE, 5×Denhardt's, 0.2% SDS, 500 μg/ml denatured salmon sperm DNA. After hybridization, the membranes were washed with 4 x SSC, 0.5% SDS at 65° C. and autoradiographed.

The subclone pDR4.7 hybridizes to two EcoRI fragments of 13.5 and 4.5 kb size and to two HindIII fragments of 10.5 and 4.4 kb size in KB-3-1 DNA when the filters are washed under low stringency conditions (4× SSC; 65° C.). Only the 13.5 kb EcoRI and 4.4 kb HindIII fragments were detectable under conditions of intermediate stringency (1 x SSC; 65° C.). All the fragments were amplified in colchicine-resistant sublines KB-8- 5-11, KB-8- 5-11-24, KB-C3 and KB-C4.

No amplification of either the band corresponding to the 13.5 kb fragment or the band corresponding to the 4.4 kb fragment was detected in the revertant subline KB-Cl-R1. Unlike the colchicine-selected sublines, the subline KB-V1, selected in vinblastine, shows amplification of only the 13.5 kb EcoRI and the 4.4 kb HindIII bands. These two bands were also amplified in Adriamycin-resistant cells KB-A1 and KB-A2. KB-A1, in addition, contained a new amplified band of a 7 kb size in the EcoRI digest and of a 6.5 kb size in the HindIII digest. The same bands were present in KB-V1 DNA, but their intensity suggested that these bands were not amplified. No bands of this size were detected in the parental KB-3-1 DNA, suggesting that they apparently arose as a result of a DNA rearrangement.

The different patterns of amplification of the two types of bands hybridizing to the hamster mdr probe in different sublines suggested that they might correspond to two different related DNA sequences, possibly different members of a multigene family, rather than to two different parts of one contiguous hybridizing region. DNA sequences corresponding to the 13.5 kb EcoRI and 4.4 kb HindIII fragments were designated mdr1 and the sequences corresponding to the 4.5 kb EcoRI and the 10.5 kb HindIII fragments were designated mdr2.

The degree of amplification of mdr sequences in different multidrug-resistant sublines was estimated by comparing the intensity of hybridization signals from serially diluted EcoRI digests of different cellular DNAs. The estimates of the copy number of mdr sequences in different sublines are given in Table 2. In Table 2, a star indicates the rearrangement of mdr2 DNA sequences.

TABLE 2

| Cell Line | Degree of Amplification | |
|---|---|---|
| | mdr1 | mdr2 |
| KB-3-1 | 1 | 1 |
| KB-8-5-11 | 7–8 | 7–8 |
| KB-8-5-11-24 | 9 | 9 |
| KB-C3 | 20 | 20 |
| KB-C4 | 30 | 30 |
| KB-C1-R1 | 1 | 1 |
| KB-V1 | 100 | 1* |
| KB-A1 | 70 | 30* |

TABLE 2-continued

| Cell Line | Degree of Amplification | |
|---|---|---|
| | mdr1 | mdr2 |
| KB-A2 | 80 | 1 |

By comparison of Table 1 with Table 2, it may be observed that in the sublines selected for a 40–700 fold degree of resistance to colchicine, there is a general, but not precise, correlation between increases in drug resistance and in the copy number of mdr sequences. The degree of resistance may correlate more precisely with the expression of mdr RNA than with the degree of mdr gene amplification. The mdr1 and mdr2 sequences appear to be amplified to a similar degree in these cells. The loss of amplified mdr sequences in a revertant of a colchicine-resistant cell line provides strong additional evidence that mdr gene amplification underlies multidrug resistance in the highly resistant cells. The degree of amplification of mdr1 in the cells selected for resistance to vinblastine or Adriamycin appears to be higher than in the cells with a similar degree of resistance that have been selected with colchicine.

EXAMPLE 4

Figure 2:
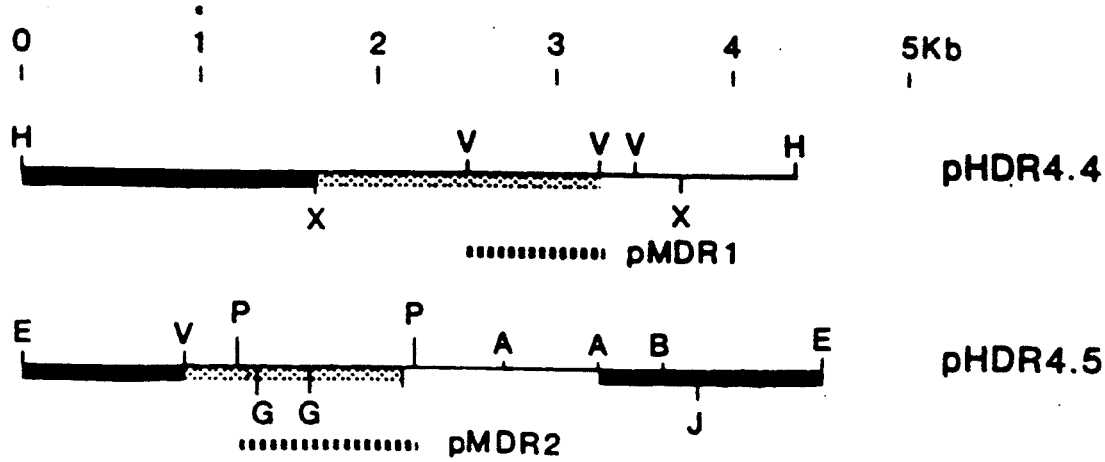
FIG. 2 illustrates partial restriction maps of the plasmid clones pHDR4.4 and pHDR4.5, respectively containing mdr1 and mdr2 sequences.

To investigate the nature of the human mdr genes, clones containing mdr1 and mdr2 sequences were isolated from the DNA of the colchicine-resistant subline KB-C3. For this purpose, two phage libraries containing complete EcoRI or HindIII digests of KB-C3 DNA were prepared. The EcoRI library was constructed by insertion into the EcoRI site of the λgtll phage vector, and the HindIII library was made by insertion into the HindIII site of Charon 28 [Young et al., *Proc. Natl. Acad. Sci. (USA)*, 80, 1194 (1983); Rimm et al., *Gene*, 12, 301 (1980)]. Both libraries were screened by plaque hybridization with the Chinese hamster pDR4.7 probe according to the procedure of Benton et al., *Science*, 196, 180 (1977). A clone containing the 4.4 kb HindIII fragment (mdr1) was isolated from the HindIII library, and a clone containing the 4.5 kb EcoRI fragment (mdr2) was isolated from the EcoRI library. Both inserts were subsequently recloned into the plasmid vector-pSP64 [Melton et al., *Nucleic Acids Res.*, 12, 7035 (1984)], giving rise to plasmid clones designated pHDR4.4 and pHDR4.5, respectively. Plasmid clone pHDR4.4 was deposited with the American Type Culture Collection, 12301 Parklawn Drive, Rockville, Md., as Deposit No. 40227 on March 21, 1986. Likewise, plasmid clone pHDR4.5 was deposited with the American Type Culture Collection, 12301 Parklawn Drive, Rockville, Md., as Deposit No. 40228 on Mar. 21, 1986. Partial restriction maps of these clones are shown in FIG. 2. In FIG. 2, sites for digestion by corresponding restriction endonucleases are identified as follows: "A", AvaI; "B", BamHI; "E", EcoRI; "G", BglII; "H", HindIII; "J", HaeII; "P", PstI; "V", PvuII; and "X", XbaI.

In FIG. 2, solid bars indicate the fragments containing highly repeated sequences. These fragments were identified by hybridization of Southern blots containing restriction digests of cloned DNA with $0.35 \times 10^5$ dpm/cm$^2$ of $^{32}$P-labeled total human genomic DNA. Dashed lines indicate the DNA sequences hybridizing to the pDR4.7 clone, as determined by Southern hybridization with the gel-purified pDR4.7 insert.

Because the pDR4.7 hamster probe was known to contain transcriptionally active sequences expressed in multidrug-resistant hamster cells [Gros et al., *Proc. Nat'l. Acad. Sci. (USA)*, supra]it seemed likely that the conserved human mdr sequences would provide convenient probes for transcription studies. The hamster pDR4.7 probe hybridized very poorly, if at all, to mRNA from multidrug-resistant human cells, and therefore could not be used as a probe for detection of mdr genes in human cells. Consequently, repeat-free fragments of both clones which hybridized to pDR4.7 were subcloned into the plasmid vector pSP64. The clone containing a 0.75 kb PvuII fragment of pHDR4.4, inserted into the SmaI site of the vector, was designated pMDR1. The clone containing a 1.0 kb PstI fragment of pHDR4.5, inserted into the PstI site of the vector, was designated pMDR2. These two clones were found to cross-hybridize with each other under conditions of low hybridization stringency providing additional evidence that mdr1 and mdr2 represent related DNA sequences.

EXAMPLE 5

To determine whether the rearranged bands in KB-V1 and KB-A1 correspond to mdr1 or mdr2, DNA from different sublines was digested with HindIII and hybridized to either hamster pDR4.7 probe or to the human pMDR1 or pMDR2 probes. Hybridization with the gel-purified insert of the plasmid pDR4.7 was done under conditions of low stringency ($4 \times$ SSC, 0.5% SDS at 65° C.). The same blot was then rehybridized with gel-purified inserts of the plasmids pMDR1 and pMDR2 under high stringency conditions ($0.1 \times$ SSC, 0.5% SDS at 65° C.) so that the signal resulting from cross-hybridization of mdr1 and mdr2 sequences was minimized.

This experiment demonstrated that rearranged bands in both KB-A1 and KB-V1 sublines correspond to mdr2. The mobility of the new bands appears to be identical in several different restriction digests of KB-V1 and KB-A1 DNA, indicating that a similar rearrangement may have occurred in both independently selected sublines. However, while the rearranged bands are amplified in KB-A1, they do not appear amplified in KB-V1 cells. In addition, both types of cells contain bands corresponding to the unrearranged allele of mdr2, which is not amplified. Amplification of the rearranged but not the parental mdr2 band in KB-A1 cells suggests that DNA rearrangement either preceded or occurred simultaneously with the onset of gene amplification in these cells. In the case of KB-V1, it is unclear whether mdr2 rearrangement is related to amplification of mdr1.

EXAMPLE 6

To determine whether the evolutionarily conserved regions of mdr1 and mdr2 contained transcribed sequences, pMDR1 and pMDR2 were used as probes for Northern hybridization, performed according to the procedure of Thomas, *Proc. Natl. Acad. Sci. (USA)*, 77, 5201–5205 (1980) with poly (A)+ RNA extracted from the parental KB-3-1 and multidrug-resistant KB-C2.5 cells [Akiyama et al., supra; Fojo et al., *Cancer Res.*, supra; Richert et al., supra and Shen et al., supra]under the conditions of high hybridization stringency as recited in Example 5. Poly (A)+RNA was extracted from the parental drug-sensitive KB-3-1 cells and from the colchicine-resistant KB-C2.5 subline as described in Chirgwin et al., *Biochem.*, 18, 5294 (1979). One microgram of each RNA preparation was electrophoresed in a 1.5% glyoxal agarose gel [McMaster et al., *Proc. Natl.*

*Acad. Sci. (USA)*, 74, 4835 (1977)]and transferred onto Gene Screen Plus ™ membrane as available from New England Nuclear, Boston, Mass. The membranes were hybridized with $3 \times 10^5$ dpm/cm$^2$ of pMDR1 or pMDR2 probes. Hybridization was done in 1M NaCl, 10% dextran sulphate, 1% SDS, 50% formamide, 100 μg/ml denatured salmon sperm DNA at 42° C. The membranes were washed with 0.1×SSC, 0.5% SDS at 65° C. and autoradiographed. The size of the RNA band was determined relative to the positions of 28S and 18S ribosomal RNA.

The probe pMDR1 hybridizes to an mRNA band of a 4.5 kb size which is highly expressed in the drug-resistant cells. This mRNA is not detectable in the parental KB-3-1 cells, indicating little or no expression when the probes were labelled either by nick translation or oligolabelling. No distinct bands, however, could be detected when pMDR2 was used as a probe. In addition, no bands were revealed by using other repeat-free subfragments of pHDR4.5 as probes in addition to pMDR2. While the existence of transcriptionally active sequences in other regions of mdr2 or transcription of mdr2 sequences at a very low level cannot be excluded by these results, transcription of the amplified region of mdr2 homologous to the Chinese hamster mdr gene is not detected by Northern hybridization.

Amplification and over expression of DNA sequences homologous to the Chinese hamster mdr gene in multidrug-resistant human KB carcinoma cells suggests that a similar mechanism may be responsible for multidrug resistance in both human and rodent cells. The nature of the proteins encoded by mdr genes is still unknown. The size of mdr1 mRNA is consistent with the possibility that it may code for a 170 kd glycoprotein overexpressed in various multidrug-resistant cell lines [Biedler et al., supra; Ling et al., supra; Ramu et al., supra; Beck et al., supra; Kartner et al., *Science*, 221, 1285 (1983); Debenham et al., *Mol. Cell. Biol.*, 2, 881 (1982); Robertson et al., *Mol. Cell. Biol.*, 4, 500 (1984)]. It is also unknown whether the same mechanism is utilized in the development of multidrug resistance by human tumor cells in vitro and in the course of chemotherapy. The availability of cloned probes which detect transcription of mdr DNA in human cells makes it possible now to investigate expression of these sequences in clinical samples of multidrug-resistant tumors.

EXAMPLE 7

In order to examine levels of expression of mdr1 sequences during the development of multidrug resistance, multidrug-resistant sublines of human KB carcinoma cells and two other human multidrug resistant cell lines of different origin were studied.

Agents used in selecting different sublines in multiple steps were colchicine, Adriamycin and vinblastine. In the first two steps of colchicine selection, clones were only obtained if the cell populations were first mutagenized with ethylmethane sulfonate (EMS). Similarly, KB cell lines selected independently for resistance to Adriamycin or vinblastine [Akiyama et al., supra; Fojo et al., *Cancer Res.*, supra; Richert et al., supra; and Shen et al., supra]were obtained only after mutagenesis with EMS in the first step. Subsequent selection, up to very high levels of resistance, was possible without mutagenesis, and occurred at high frequency.

The isolation and some properties of the human multidrug resistant KB carcinoma cell lines has been previously described in Akiyama et al., supra; Fojo et al., *Cancer Res.*, supra; and Richert et al., supra. The KB cell lines used in this study, the manner of their selection, and their relative resistance to various drugs, are shown in Table 3. CEM is a cell line described in Beck in *Advances in Enzyme Regulation*, 22, G. Weber, ed. (Pergamon Press, Oxford, 1984), 207, and 2780 is a cell line described in Rogan et al., *Science*, 224, 994 (1984).

To determine the extent to which mdr1 sequences were expressed in these cell lines and the size of the corresponding RNAs, a Northern hybridization was performed with total RNA and poly (A)+-RNA from these cells. A 4.5 kilobase RNA, which migrates just below the 28S ribosomal RNA marker, was clearly visible in all the lanes containing either total or poly (A)+ RNA from the resistant lines but was not seen in any of the sensitive cell lines.

Slot blot hybridization of total RNA was used to quantitate the expression of mdr1 in various sensitive and resistant cell lines. RNA prepared as previously described above was applied to filters using a Schleicher and Schuell slot blot apparatus or by blotting after electrophoresis in 1% agarose containing 13.4% formaldehyde. A gel-purified insert from the pMDR1 clone was $^{32}$P-labeled for use as a probe. Nitrocellulose filters were baked and preincubated for 4–6 hours at 42° C. in 50% formamide, 5×SSC, 10×Denhardt's solution, 0.1% SDS and 100 μg/ml salmon sperm DNA. Filters were hybridized overnight in the above solution containing $^{32}$P-labeled probe. Filters were washed 3 times for 10 minutes at room temperature in 2×SSC, 0.1% SDS and 3 times for 20 minutes at 50° C. in 0.1× SSC, 0.1% SDS. Levels of mdr1 expression were determined by densitometry of the autoradiograms. Tracings of peaks were cut out and weighed and compared to the KB-8 peak which was arbitrarily assigned a value of 1. The results are presented in Table 3 along with the relative drug resistances of the human leukemic lymphoblast cell lines, and the human ovarian cancer cell lines used in the study. In Table 3, ND is an abbreviation for "none detected".

TABLE 3

| Cell Line | Selecting Agent | Relative Resistance to | | | mdr1 mRNA Expression |
|---|---|---|---|---|---|
| | | Col | Adr | Vbl | |
| KB-3-1 | parental KB | 1 | 1 | 1 | ND |
| KB-8 | colchicine, 5 ng/ml | 2.1 | 1.1 | 1.2 | 1 |
| KB-8-5 | colchicine, 10 ng/ml | 3.8 | 3.2 | 6.3 | 3 |
| KB-8-5-11 | colchicine, 100 ng/ml | 40 | 23 | 51 | 80 |
| KB-C1 | colchicine, 1 μg/ml | 260 | 160 | 96 | 270 |
| KB-C1-R1 | revertant of KB-C1 | 6 | 3 | 4 | 1 |
| KB-C1.5 | colchicine, 1.5 μg/ml | 320 | — | 140 | 340 |
| KB-C6 | colchicine, 6 μg/ml | 2,100 | 320 | 370 | 820 |
| KB-A1 | Adriamycin, 1 μg/ml | 19 | 97 | 43 | 270 |
| KB-V1 | vinblastine, 1 μg/ml | 170 | 420 | 210 | 320 |
| CEM | parental leukemic | 1 | 1 | 1 | ND |
| CEM-Vlb$_{100}$ | vinblastine | 45 | 120 | 420 | 250 |
| 2780 | parental, ovarian | 1 | 1 | 1 | ND |
| 2780-Ad | Adriamycin | — | 170 | 15 | 260 |

As shown in Table 3, there was a good correlation between extent of multidrug resistance and the level of mdr1-specific mRNA. As can also be seen in Table 3, there is little or no expression of the mdr1 sequences in parental, drug-sensitive cell lines, but increasing expression occurs as the cell lines become more resistant to drugs. A revertant cell line, KB-Cl-Rl, subcloned in the absence of colchicine from the colchicine-resistant cell line KB-Cl, still expresses mdr1 sequences at reduced levels consistent with its low level of multidrug resistance.

It is not possible to calculate the exact extent of increased expression in the resistant cell lines relative to the parental line, since the hybridization signal from the parental RNA was too weak. However, the extent of expression relative to the KB-8 cell line has been calculated and these data are shown in Table 3. Expression appears to correlate well with increasing drug-resistance for every step of selection in KB cells and reaches very high levels in our most resistant KB cell lines.

The data summarized in Table 3 indicate that two other human cell lines of different origin, selected for multidrug resistance, also express high levels of the 4.5 kb mRNA. Very little or no expression of this RNA was detected in the parental cell lines. The human leukemic lymphoblast cell line CEM (A.T.C.C. CCL119) and its resistant derivatives CEM-VLB$_{100}$, selected for resistance to vinblastine (gift of W. Beck, St. Jude's Hospital) (Beck, supra.) and the ovarian cell line 2780 and its resistant derivative 2780-Ad, selected for resistance to Adriamycin (gift of T. Hamilton and R. Ozols, National Institutes of Health) (Rogan et al., supra) both showed high levels of expression of the 4.5 kb mRNA. Because even low levels of cellular multidrug-resistance may result in clinically refractory tumors, expression of mdr1 mRNA in sublines having a low level (2-6 fold) of relative drug resistance but not in the parental drug-sensitive cell lines is of particular interest. In this regard the results presented in Table 3 indicate that quantitation of mdr1 mRNA expression may potentially be used for diagnosis of multidrug resistance in clinical tumor specimens.

EXAMPLE 8

To compare the levels of mdr1 mRNA expression with the extent of amplification of the genomic mdr1 sequences genomic DNA was isolated from all of the cell lines described in Example 6. Following digestion with HindIII, amplification of mdr1 was examined by Southern blot analysis.

DNA, prepared as previously described in Example 3, was digested with HindIII and electrophoresed in 0.8% agarose gels before Southern transfer to Gene Screen Plus ™ (New England Nuclear). The blots were hybridized with the pMDR1 probe for 18 hours at 42° C. in 50% formamide, 5×SSC, 1% SDS with 100 μg/ml salmon sperm DNA. The blots were then washed with 2×SSC at room temperature for 10 minutes, 2×SSC, 1% SDS at 42° C. for 60 minutes and 0.1×SSC at room temperature for 60 minutes prior to autoradiography.

No amplification of mdr1 was found in the KB cell lines with low levels of resistance (KB-8, KB-8-5 and the revertant subline, KB-Cl-Rl), even though these cell lines expressed increased levels of mdr1 mRNA. Increased expression of mdr1 sequences in human cells may therefore occur prior to gene amplification. Amplification of the mdr1 gene was detected in highly resistant sublines of KB cells selected in colchicine, vinblastine or Adriamycin, as well as in CEM-VLB100 and 2780-Ad cell lines. In the latter two sublines, the degree of gene amplification was estimated by densitometry to be approximately 5–10 fold for 2780-Ad and 10–15 fold for CEM-VLB$_{100}$.

In all cases, the increase in mRNA expression was clearly greater than the extent of amplification. These results suggest that the evolution of these lines involved a step or steps in which expression was increased out of proportion to gene amplification. A similar dissociation of amplification and expression of the dhfr gene has been reported for human cancer cells selected for resistance to methotrexate in vitro. [Frei et al., *Proc. Natl. Acad. Sci. (USA)*, 81, 2873 (1984); Wolman et al., *Proc. Natl. Acad. Sci. (USA)*, 80, 807 (1983).]The development of multidrug resistance in human KB cells differs in this respect from Chinese hamster V79 cells where a low (5–7 fold) degree of relative drug resistance is accompanied by 5–10 fold amplification of mdr DNA [Roninson et al., supra; and Gros et al., supra].

These studies demonstrate a correlation between expression of the mdr1 gene and the development of resistance to multiple agents in five independently-derived human cell lines of different origins selected for resistance to different cytotoxic drugs. Expression of mdr1 may therefore represent a common mechanism of multidrug resistance in human cell lines. Increased expression of mdr1 in at least some cases occurs initially without gene amplification and may be a prerequisite for the development of multidrug resistance. This observation may be especially relevant for the analysis of the role of the mdr1 gene in the development of multidrug resistance by human tumors in the course of chemotherapy and may have diagnostic potential. Since the tumor cells are expected to have a relatively low degree of resistance, such an analysis may involve quantitation of mdr1 RNA expression rather than gene amplification in tumor samples.

EXAMPLE 9

The segment of the mdr1 gene cloned into pMDR1 was sequenced by the chemical degradation procedure [Maxam et al., *Meth. Enzymol.*, 65, 499, (1980)]and the enzymatic chain-termination sequencing technique [Sanger et al., *Proc. Natl. Acad. Sci. USA*, 74, 5463, (1977)]using supercoiled plasmid DNA as a template [Zagursky et al., *Gene Anal. Techn.*, 2, 89, (1985)]. To facilitate sequencing, pMDR1 was mapped with HaeIII and RsaI and individual 220–400 bp fragments of pMDR1 were subcloned into a pUC18 plasmid vector (Bethesda Research Laboratories, Rockville, Md.). The sequence of pMDR1 was confirmed by sequencing both strands. The complete sequence of pMDR1 is presented in Table 4. Comparison with the sequence of the corresponding cDNA clones in Example 10 below indicated that pMDR1 includes segments of two protein-coding sequences (exons), comprising nucleotides 1–111 and 653–807, and an intervening sequence (intron) which is not expressed as mRNA and which comprises nucleotides 112–652. Table 4 shows that amino acid sequence corresponding to the exons within pMDR1. This amino acid sequence therefore defines a segment of the mdr1 protein product.

EXAMPLE 10

Figure 3:
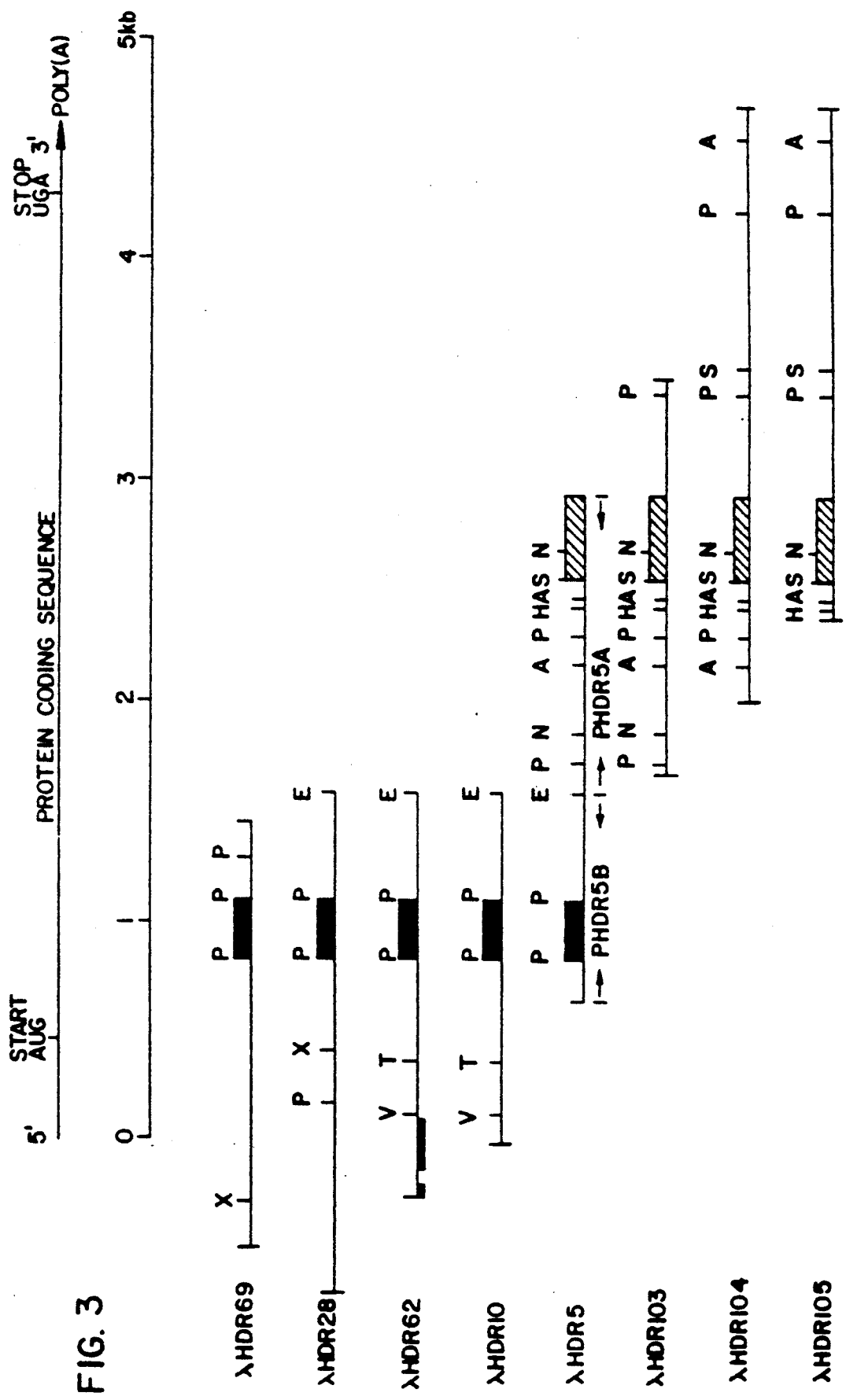
FIG. 3 illustrates partial restriction maps of phage cDNA clones λHDR5, λHDR10, λHDR62, λHDR28, λHDR69A, λHDR103 λHDR104 and λHDR105 containing mdr1 sequences.

In order to isolate cDNA clones of the mdr1 gene, poly(A)+ RNA was isolated as described in Chirgwin et al., *Biochemistry*, 18, 5294 (1979) and Aviv et al., *Proc. Natl. Acad. Sci. (USA)*. 69, 1408 (1972) from the subline KB-C2.5, selected with colchicine. A cDNA library was constructed using the steps of synthesizing double-stranded cDNA, blunt ending, attachment of EcoRI linkers and insertion into the phage vector λgt11 [Young and Davis, supra; Huynh et al., in: DNA Cloning Techniques: A Practical Approach, D. Glover, ed., IRL Press, Oxford, (1985)]. The cDNA library was screened by plaque hybridization (Benton et al., supra) with the pMDR1 probe. Approximately 120 positive clones were isolated. The inserts from five of these clones (λHDR5, λHDR10, λHDR28, λHDR62 and λHDR69) were re-cloned into plasmid vectors pGEM1 and pGEM4 (Promega Biotec). The partial restriction maps of these clones are shown in FIG. 3. DNA from λHDR5 was treated with EcoRI which generated two fragments, designated 5A and 5B. The fragments were subcloned into pGEM1 at its EcoRI site to give plasmids pHDR5A and pHDR5B which were deposited with the American Type Culture Collection, 12301 Parklawn Drive, Rockville, Md., on Mar. 18, 1986, and which received the respective accession numbers ATCC 67040 and ATCC 67041. Similarly, λHDR10 was treated with EcoRI and cloned into the EcoRI site of pGEM1 to produce pHDR10 which was deposited with the American Type Culture Collection, 12301 Parklawn Drive, Rockville, Md., on Mar. 18, 1986, as Deposit No. 67042.

To isolate the remaining portion of mdr1 cDNA, a fragment of the clone λHDR5, indicated with a striped bar in FIG. 3, was used to screen the same cDNA library. The inserts from three of the positive clones, designated λHDR103, λHDR104 and λHDR105, were re-cloned into the EcoRI sites of plasmid vectors pGEM1 and pGEM4, giving rise to plasmids designated pHDR103, pHDR104 and pHDR105, respectively. The plasmid pHDR104 was deposited with the American Type Culture Collection, 12301 Parklawn Drive, Rockville, Md., on Jul. 16, 1986, as Deposit No. 67156.

A comparison of the restriction maps of individual clones indicates divergence in the cDNA structure among, for example, clones λHDR10, λHDR28 and λHDR69. The most highly conserved region among these clones is represented by a 270 bp PvuII fragment, which corresponds to the exon regions of pMDR1 and is indicated with a solid bar above the lines in FIG. 3. The variant sequences specific to clones λHDR62 and λHDR105 were detected by DNA sequencing, and they are shown as solid bars underneath the corresponding lines in FIG. 3. In FIG. 3, sites for digestion by corresponding restriction endonucleases are identified as follows: "A", AccI; "E", EcoRI; "H", HindIII; "N", XmnI; "P", PvuII; "S", StuI; "T", SstI; "V", AvaI; and "X", XbaI.

The cDNA clones λHDR10, λHDR5 and λHDR104 were sequenced in their entirety using the methods of subcloning the inserts into an M13 phage vector [Messing, *Meth. Enyzmol.*, 101, 20, 1983], generating a series of overlapping deletion subclones [Henikoff, *Gene*, 28, 351, 1984]and determining their DNA sequence by the enzymatic chain-termination sequencing techniques [Sanger et al., supra]. A part of the cDNA sequence was determined by specific-primer-directed DNA sequencing [Strauss et al., *Anal. Biochem.*, 154, 353 1986]using supercoiled plasmid DNA as a template [Zagursky et al., supra]. The overlapping regions of clones λHDR10, λHDR5 and λHDR104 were found to be identical, and therefore, these clones are assumed to represent different parts of the same cDNA. The combined cDNA sequence of clones λHDR10, λHDR5 and λHDR104 is shown in Table 5. This table also shows the amino acid sequence of mdr1 gene product, derived from the same cDNA sequence.

Analysis of the amino acid sequence presented in Table 5 indicates that the mdr1 gene product is likely to be a transmembrane protein. This protein may consist of two approximately equal parts, with a considerable sequence homology to each other, indicating that the mdr1 gene has likely evolved as a result of an internal duplication. Each half of the protein consists of a hydrophobic and a hydrophilic portion. Each of the hydrophobic portions includes six transmembrane domains, as determined by the algorithm of Eisenberg et al. [*J. Mol. Biol.*, 179, 125–142 (1984)]. Both hydrophilic portions contain two regions that share a high level of amino acid homology with the ATP-binding sites of several known enzymes. The best homology has been observed with the ATP-binding sites of peripheral membrane components of bacterial periplasmic binding protein-dependent transport systems [Higgins et al., *EMBO J.*, 4, 1033–1040, (1984)]. The presence of the transmembrane domains and potential glycosylation sites within the protein sequence is consistent with the mdr1 protein being related to the P-glycoprotein, which is described above.

Analysis of the DNA and protein sequence information presented in Table 5 by the algorithm of Eisenberg et al., supra, may be used to predict the protein regions that are located on the outside of the cell membrane. These protein regions may be produced either by chemical synthesis or by expression in the appropriate vector systems, and may be used to raise antibodies against cells that express the mdr1 gene product, as described in Example 11.

EXAMPLE 11

The recombinant plasmids pMDR1 and pMDR2, as well as different individual fragments of recombinant plasmids pHDR4.4 and pHDR4.5, or the latter plasmids as a whole, or cDNA clones λHDR5, λHDR10, λHDR62, λHDR28 and λHDR69, or other sequences according to the present invention, may be used as diagnostic tools for detection of human tumor cells resistant to chemotherapeutic drugs. These plasmids may be labeled directly with a radioactive isotope, according to the procedures of Rigby et al., *Mol. Biol.*, 113, 237–251 (1977) or Feinberg et al., *Anal. Biochem.*, 132, 6–13 (1983), for example. Alternatively, the plasmids may be labelled with a non-radioactive chemical tag, for example, according to the procedure in Leary et al., *Proc. Natl. Acad. Sci. (USA)*, 80, 4045–4049 (1983). The plasmids may also be used to direct synthesis of labeled RNA probes [e.g., according to the procedure in Melton et al., *Nucleic Acids Res.*, 12, 7035–7055 (1984)]. The labeled probes may then be used to detect the presence of homologous RNA sequences in tumor cells either by the Northern hybridization procedure [according to Thomas, *Proc. Natl. Acad. Sci. (USA)*, 77, 5201–5205 (1980)]or by dot blot or slot blot hydridization [according to Kafatos et al., *Nucleic Acids Res.*, 7, 1541–1552 (1979) and Brown et al., *Mol. Cell. Biol.*, 3, 1097–1107 (1983)], or by in situ hybridization techniques [e.g., those according to the procedures of Brahic et al., *Proc. Natl. Acad. Sci. (USA)*, 75, 6125–6129

(1978)]. It is anticipated that in situ hybridization will provide a particularly sensitive method for detection of a small number (1 in 1000 or fewer) of multidrug-resistant cells within a biopsy.

The mdr clones may be used to obtain polyclonal or monoclonal [Yelton et al., *Ann. Rev. Biochem.*, 50, 657-680 (1981)]antibodies against mdr gene products using either of two strategies.

The first strategy involves determination of the cDNA sequences of mdr genes, as described in Example 10. The cDNA sequence may be used to deduce the corresponding protein sequence. Peptides corresponding to different parts of mdr proteins, and preferably comprising at least 15-20 amino acid residues, may be chemically synthesized by solid-phase methods [Marglin et al., *Ann. Rev. Biochem.*, 39, 841-866 (1970)]. Such peptides may then be used to elicit specific polyclonal and monoclonal antibodies [Lerner, *Nature*, 299, 592-596 (1982); Niman et al., *Proc. Natl. Acad. Sci. (USA)*, 80, 4949-4953 (1983)]. The availability of the full-length mdr1 cDNA sequence, as shown in Table 5, greatly facilitates the design of potentially immunogenic peptides, corresponding to different regions of the mdr1 protein, including the potential extracytoplasmic domains.

The second strategy involves expression of either complete or partial mdr gene products in bacteria, yeast or mammalian expression systems using plasmid, phage or viral expression vectors [Vieira et al., *Gene*, 19, 259-268 (1982); Young et al., *Proc. Natl. Acad. Sci. (USA)*, 80, 1194-1198 (1983); Bitter et al., *Gene*, 32, 263-274 (1984); Cepko et al., *Cell*, 37, 1053-62 (1984); and Gorman et al., *Mol. Cell. Biol.* 2, 1044-1051 (1982)]. The expressed proteins may be purified and used in a vaccine or to raise specific antibodies. Antibodies against the mdr gene products may be used as the alternative diagnostic tools for detection of drug-resistant cells. Finally, such antibodies may potentially be used as a basis for a new strategy of cancer immunotherapy. This strategy may involve, for example, conjugation of anti-mdr antibodies with radioactive isotopes or chemical toxins in order to specifically eliminate multidrug-resistant tumor cells. This approach may be particularly efficient if used in combination with chemotherapy. Alternatively, the binding of anti-mdr antibodies to cells expressing mdr gene products, even in the absence of antibody-mediated cytotoxicity, may be sufficient to reverse the multidrug-resistant phenotype and may therefore render tumor cells susceptible to the cytocidal action of the chemotherapeutic drugs.

In addition, complete or partial mdr gene products may be used as a vaccine to elicit an immune reaction in a patient against multidrug resistant tumor cells.

Although the present invention has been described in terms of preferred embodiments, it is understood that variations and modifications will occur to those skilled in the art upon consideration of the present invention. Therefore, it is intended that all such equivalent variations and modifications should come within the scope of the invention as claimed.

What is claimed is:

1. An isolated nucleic acid of the human mdr1 or mdr2 gene, or the complement thereof, selected from the group consisting of:
   a) a polynucleotide comprising a continuous sequence of nucleotides as set forth in FIG. 4 or the RNA equivalent thereof;
   b) a polynucleotide comprising a continuous sequence of nucleotides as set forth in FIG. 5 or the RNA equivalent thereof;
   c) a polynucleotide comprising the DNA insert present in pHDR4.4 (ATCC 40227) or the RNA equivalent thereof;
   d) a polynucleotide comprising the DNA insert present in pHDR4.5 (ATCC 40228) or the RNA equivalent thereof;
   e) a polynucleotide comprising the DNA insert present in pHDR5A (ATCC 67040) or the RNA equivalent thereof;
   f) a polynucleotide comprising the DNA insert present in pHDR5B (ATCC 67041) or the RNA equivalent thereof;
   g) a polynucleotide comprising the DNA insert present in pHDR10 (ATCC 67042) or the RNA equivalent thereof; and
   h) a polynucleotide comprising the DNA insert present in pHDR104 (ATCC 67156) or the RNA equivalent thereof.

2. A nucleic acid probe, having a label associated with said probe, derived from an isolated nucleic acid of the human mdr1 or mdr2 gene, or the complement thereof, selected from the group consisting of:
   a) a polynucleotide comprising a continuous sequence of nucleotides as set forth in FIG. 4 or the RNA equivalent thereof;
   b) a polynucleotide comprising a continuous sequence of nucleotides as set forth in FIG. 5 or the RNA equivalent thereof;
   c) a polynucleotide comprising the DNA insert present in pHDR4.4 (ATCC 40227) or the RNA equivalent thereof;
   d) a polynucleotide comprising the DNA insert present in pHDR4.5 (ATCC 40228) or the RNA equivalent thereof;
   e) a polynucleotide comprising the DNA insert present in pHDR5A (ATCC 67040) or the RNA equivalent thereof;
   f) a polynucleotide comprising the DNA insert present in pHDR5B (ATCC 67041) or the RNA equivalent thereof;
   g) a polynucleotide comprising the DNA insert present in pHDR10 (ATCC 67042) or the RNA equivalent thereof; and
   h) a polynucleotide comprising the DNA insert present in pHDR104 (ATCC 67156) or the RNA equivalent thereof.

3. A polynucleotide of claim 1, comprising a polynucleotide fragment selected from the group consisting of a)-h), inclusive.

4. A nucleic acid probe of claim 2, wherein said isolated nucleic acid comprises a polynucleotide fragment selected from the group consisting of a)-h), inclusive.

5. An isolated nucleic acid comprising nucleotide positions 1 through 111 or 653 through 807 of FIG. 4.

6. An isolated nucleic acid comprising nucleotide positions 425 through 4267 of FIG. 5.

7. A nucleic acid probe, having a label associated with said probe, derived from an isolated nucleic acid comprising nucleotide positions 1 through 111 or 653 through 807 of FIG. 4.

8. A nucleic acid probe, having a label associated with said probe, derived from an isolated nucleic acid comprising nucleotide positions 425 through 4267 of FIG. 5.

* * * * *